(12) United States Patent
Merbl et al.

(10) Patent No.: US 11,035,858 B2
(45) Date of Patent: Jun. 15, 2021

(54) METHODS OF ISOLATING BARREL-LIKE PROTEASES AND IDENTIFYING PEPTIDES PROCESSED THEREBY

(71) Applicant: Yeda Research and Development Co. Ltd., Rehovot (IL)

(72) Inventors: Yifat Merbl, Rehovot (IL); Hila Wolf-Levy, Rehovot (IL); Yishai Levin, Rehovot (IL); Bareket Dassa, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 222 days.

(21) Appl. No.: 16/082,296

(22) PCT Filed: Mar. 17, 2017

(86) PCT No.: PCT/IL2017/050339
§ 371 (c)(1),
(2) Date: Sep. 5, 2018

(87) PCT Pub. No.: WO2017/158610
PCT Pub. Date: Sep. 21, 2017

(65) Prior Publication Data
US 2019/0033312 A1     Jan. 31, 2019

(30) Foreign Application Priority Data

Mar. 17, 2016 (IL) ......................... 244649

(51) Int. Cl.
| | | |
|---|---|---|
| *G01N 33/00* | (2006.01) | |
| *G01N 33/573* | (2006.01) | |
| *C12Q 1/37* | (2006.01) | |
| *G01N 33/50* | (2006.01) | |

(52) U.S. Cl.
CPC ............ *G01N 33/573* (2013.01); *C12Q 1/37* (2013.01); *G01N 33/502* (2013.01); *G01N 2333/96425* (2013.01)

(58) Field of Classification Search
CPC ........... C12Q 1/37; G01N 2333/96425; G01N 33/502; G01N 33/573
See application file for complete search history.

(56) References Cited

U.S. PATENT DOCUMENTS

| | | |
|---|---|---|
| 2013/0144541 A1 | 6/2013 | Rychnovsky et al. |
| 2016/0109453 A1 | 4/2016 | Weinhausel |
| 2018/0371550 A1 | 12/2018 | Komurov |

FOREIGN PATENT DOCUMENTS

| | | |
|---|---|---|
| EP | 1005483 | 6/2000 |
| WO | WO 2005/011619 | 2/2005 |
| WO | WO 2017/158610 | 9/2017 |

OTHER PUBLICATIONS

Smith et al. ReCLIP (Reversible Cross-Link Immuno-Precipitation): An Efficient Method for Interrogation of Labile Protein Complexes. 2011. PLoS ONE Jan. 2011 I vol. 6 I Issue 1: e16206 (Year: 2011).*
Wang et al. Mass Spectrometric Characterization of the Affinity-Purified Human 26S Proteasome Complex Biochemistry 2007, 46, 3553-3565. (Year: 2007).*
International Preliminary Report on Patentability dated Sep. 27, 2018 From the International Bureau of WIPO Re. Application No. PCT/IL2017/050339. (8 Pages).
International Search Report and the Written Opinion dated May 31, 2017 From the International Searching Authority Re. Application No. PCT/IL2017/050339. (14 Pages).
Office Action dated Nov. 30, 2016 From the Israel Patent Office Re. Application No. 244649. (7 Pages).
Search Report dated Nov. 20, 2016 From the Israel Patent Office Re. Application No. 244649. (1 Page).
Hunt et al. "Characterization of Peptides Bound to Class I MHC Molecule HLA-A2.1 by Mass-Spectrometry", Science, 255(5049): 1261-1263, 1992.
Martinez-Maqueda et al. "Extraction/Fractionation Techniques for Proteins and Peptides and Protein Digestion", Proteomics in Foods: Principles and Applications, Food Microbiology and Food Safety, 2(Chap.2): 21-50, Nov. 30, 2012.
Smith et al. "ReCLIP (Reversible Cross-Link Immuno-Precipitation): An Efficient Method for Interrogation of Labile Protein Complexes", PLoS ONE, 6(1): e16206-1-e16206-9, Jan. 20, 2011.
Steers et al. "Isolation and Purification of Proteasomes From Primary Club", Current Protocols in Immunology, XP055374766, 107(Suppl.): 16.4.1-16.4.20, Nov. 3, 2014. Abstract, p. 16.4.2-16. 4.3, 16.4.7-16.4.9, 16.4.16.
Wang et al. "Mass Spectrometric Characterization of the Affinity-Purified Human 26S Proteasome Complex", Biochemistry, XP055374794, 46(11): 3553-3565, Published on Web Feb. 27, 2007. Abstract, p. 3555, r-h Col., Last Para—p. 3556, l-h col., p. 3558, r-h Col.—p. 3559, l-h Col.
Zaman et al. "Dithiothreitol (DTT) Acts as a Specific, UV-Inducible Cross-Linker in Elucidation of Protein-RNA Interactions", Molecular & Cellular Proteomics, XP055374768, 14(12): 3196-3210, Published Online Oct. 8, 2015. Abstract.
Wolf-Levy et al. "Revealing the Cellular Degradome by Mass Spectrometry Analysis of Proteasome-Cleaved Peptides", Nature Biotechnology, 36(11): 1110-1116, Advance Online Publication Oct. 22, 2018.

(Continued)

*Primary Examiner* — James H Alstrum-Acevedo
*Assistant Examiner* — Mercy H Sabila

(57) ABSTRACT

A method of isolating barrel-like proteases is disclosed. The method comprising isolating barrel-like proteases from a biological sample containing the barrel-like proteases under conditions that maintain the content of the barrel-like protease-processed peptides in the barrel-like proteases upon isolation. A method of isolating barrel-like protease-processed peptides and a method of identifying barrel-like protease-processed peptides are also disclosed.

23 Claims, 9 Drawing Sheets

(6 of 9 Drawing Sheet(s) Filed in Color)

(56) References Cited

OTHER PUBLICATIONS

Invitation to Pay Additional Fees, Communication Relating to the Results of the Partial International Search and the Provisional Opinion dated Jun. 8, 2020 From the International Searching Authority Re. Application No. PCT/IL-2020/050303. (10 Pages).

Welk et al. "Analyzing the Role of Proteasome Activator 200 (PA200) in Lung Cancer", European Respiratory Journal, XP055698577, 52(S62): pa2849, Sep. 15, 2018.

Communication Pursuant to Article 94(3) EPC dated Sep. 1, 2020 From the European Patent Office Re. Application No. 17719351.3. (6 Pages)

International Search Report and the Written Opinion dated Jul. 29, 2020 From the International Searching Authority Re. Application No. PCT/IL2020/050303. (18 Pages).

* cited by examiner

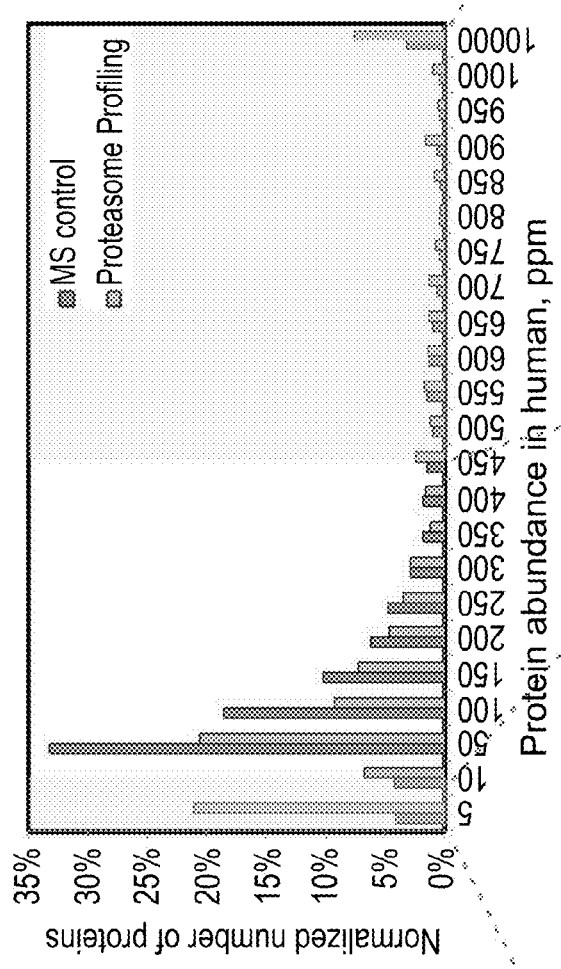
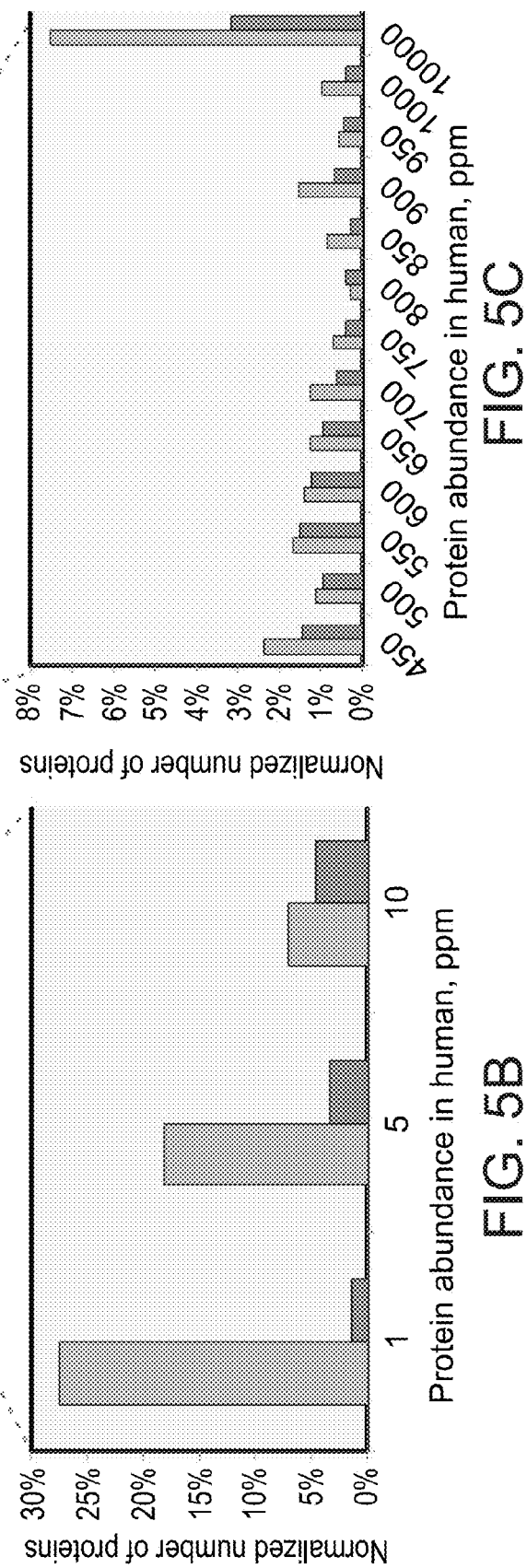
FIG. 5A
FIG. 5B
FIG. 5C

METHODS OF ISOLATING BARREL-LIKE PROTEASES AND IDENTIFYING PEPTIDES PROCESSED THEREBY

RELATED APPLICATIONS

This application is a National Phase of PCT Patent Application No. PCT/IL2017/050339 having International filing date of Mar. 17, 2017, which claims the benefit of priority of Israel Patent Application No. 244649, filed on Mar. 17, 2016. The contents of the above applications are all incorporated by reference as if fully set forth herein in their entirety.

FIELD AND BACKGROUND OF THE INVENTION

The present invention, in some embodiments thereof, relates to methods of isolating barrel-like proteases and identifying peptides processed thereby.

The proteasome system is the main proteolytic machinery of the cell. In the last few decades since its' discovery, it became clear that degradation by the proteasome system is a highly-regulated process implicated in numerous cellular events including transcription, differentiation, proliferation, cell death and more. Alterations in this process are often related to different pathologies such as malignancies and neurodegenerative disorders. Moreover, specific drugs that target the proteasome are already used in the clinic and present novel therapeutic strategies. The pool of proteins that are targeted for degradation at a specific cell-state can thus define significant information including activation or aberration of cellular processes, alterations in protein levels, expression of mutants and more. Therefore, analysis of proteasomal degradation can provide substantial insights into cellular programs and state and present novel therapeutic possibilities.

The proteasome is a mega protein complex of approximately 2.5 MDa, which can be divided, based on biochemical and functional properties, into two sub-complexes consisting of catalytic and regulatory subunits. The core 20S subunit comprises the proteolytic element, while the 19S regulatory subunit is responsible for the recognition and transport of substrates into the 20S core where they are degraded. Structurally, the 20S catalytic core is a hollow barrel composed of four stacked rings of seven alpha and beta subunits. Proteasome assembly begins with spontaneous chaperone-mediated formation of the alpha stacked rings, which serve as templates for the association of complementary beta rings. Following completion, each pair of alpha-beta stacked rings dimerize to form the latent core particle that binds to pre-assembled 19S particles to form the mature 26S proteasome. The 19S regulatory particle is a large complex of about 1 MDa and consists of at least 19 different subunits forming the "lid" and "base" of the subunit, including resident ATPases and deubiquitinating enzymes. The most common form of targeting proteins to the proteasome involves their covalent conjugation to poly-ubiquitin chains on lysine residues. As ubiquitin itself has seven lysine residues, several topologies of ubiquitylation can exist. While K48 poly-ubiquitin chains are typically correlated with proteasomal degradation, other lysine ubiquitin chains have also been implicated in proteasomal targeting. Upon binding to the 19S subunit, ubiquitin is cleaved off and the target protein is translocated into the core 20S subunit where it is degraded.

Mass spectrometry (MS) analysis has provided tremendous achievements in the ability to decode the proteasome and identify global changes of proteins under different conditions in health and disease. Most types of analyses are done by processing the biological samples in bulk, digesting the proteins into peptides using purified enzymes such as trypsin and chemotrypsin and generating the list of proteins that the sample contains based on their ionization and mass that were identified by the MS. Two major difficulties in MS analysis are the dynamic range of proteins abundance in the cell and the complexity of tissues which contain thousands of different proteins at once. Thus, proteins that are in low abundance in the cell or ones that are rapidly turning over, such as transcription factors, are often hard to detect by MS analysis and require further steps of enrichments in order to be detected and quantified by MS. Even more so sampling of proteins by MS analysis reflects their abundance in the tissue but does not infer on their activity or function in a given time.

Another approach to identify endogenous peptides is the analysis of peptides presented on MHC complexes. In this manner, MHC complexes are isolated and separated from their cargo, which is analyzed by mass spectrometry (Hunt et al. (1992) *Science* vol. 255 (5049) p. 1261-1263). Still, caveats of this approach include relatively low sensitivity, requiring a very large number of cells and a bias towards highly-abundant proteins. Moreover, only extracellular peptides bound to the presenting molecule are examined.

There is thus a widely recognized need for a tool that analyzes protein dynamics in a cell and for elucidating proteome dynamics based thereon.

Additional background art includes:
Steers et al. 2014 Current Immunology 107:16.4.1-20.

SUMMARY OF THE INVENTION

According to an aspect of some embodiments of the present invention there is provided a method of isolating a barrel-like proteases, the method comprising isolating barrel-like proteases from a biological sample containing the barrel-like proteases under conditions that maintain the content of the barrel-like protease-processed peptides in the barrel-like proteases upon the isolation, thereby isolating the barrel-like proteases.

According to an aspect of some embodiments of the present invention there is provided a method of isolating barrel-like protease-processed peptides, the method comprising:

(a) isolating barrel-like proteases as described herein; and (b) isolating a peptide pool from total proteinaceous pool of the isolated barrel-like proteases, thereby isolating the barrel-like protease-processed peptides.

According to an aspect of some embodiments of the present invention there is provided a method of identifying barrel-like protease-processed peptides, the method comprising:

(a) isolating the barrel-like protease-processed peptides as described herein; and (b) subjecting the barrel-like protease-processed peptides to sequence analysis, thereby identifying the barrel-like protease-processed peptides.

According to some embodiments of the invention, the conditions that maintain the content of the barrel-like protease-processed peptides in the barrel-like proteases comprise contacting the barrel-like proteases with a peptidase inhibitor.

According to some embodiments of the invention, the conditions that maintain the content of the barrel-like protease-processed peptides in the barrel-like proteases comprise a cross-linking agent.

According to some embodiments of the invention, the barrel-like protease is a proteasome.

According to some embodiments of the invention, the biological sample is from a healthy tissue or cell, malignant tissue or cell, an inflamed tissue or cell, a senescent tissue or cell, an immature tissue or cell, a senescent tissue or cell, or a pathogen infected tissue or cell.

According to some embodiments of the invention, the biological sample is selected from the group consisting of intact cells in suspension, tissue biopsy, cell-free proteasomes, exosomes and microparticles.

According to some embodiments of the invention, the cell sample comprises a body fluid, a cell line or a primary cell.

According to some embodiments of the invention, the body fluid is selected from the group consisting of whole blood, fractionated blood, serum, plasma, cerebrospinal fluid, urine, lymph fluid, and an external secretion of the respiratory, intestinal and genitourinary tracts, tears, saliva, milk, peritoneal lavage and amniotic fluid.

According to some embodiments of the invention, the biological sample comprises immune cells.

According to some embodiments of the invention, the immune cells are antigen presenting cells.

According to some embodiments of the invention, the immune cells are activated immune cells.

According to some embodiments of the invention, the immune cells are naive immune cells.

According to some embodiments of the invention, the biological sample comprises cancer cells.

According to some embodiments of the invention, the biological sample comprises pathogen-infected cells.

According to some embodiments of the invention, the biological sample comprises stem cells or progenitor cells.

According to some embodiments of the invention, the biological sample comprises senescent cells.

According to some embodiments of the invention, the isolating the barrel-like proteases is effected following cell lysis.

According to some embodiments of the invention, the isolating the barrel-like proteases is effected by immunoprecipitation using an antibody to the barrel-like protease or a protein associated therewith.

According to some embodiments of the invention, the isolating a peptide pool from total proteinaceous pool of the isolated barrel-like proteases is effected by solvent precipitation followed by solid phase extraction.

According to an aspect of some embodiments of the present invention there is provided a barrel-like protease preparation obtainable according to the method described herein.

According to an aspect of some embodiments of the present invention there is provided a peptide preparation obtainable according to the method described herein.

According to an aspect of some embodiments of the present invention there is provided a computer readable storage medium comprising an annotated sequence data of the peptide preparation.

According to an aspect of some embodiments of the present invention there is provided a method of testing an effect of a test compound or condition, the method comprising:

(a) contacting a biological sample comprising barrel-like proteases with the test compound; and subsequently.

(b) identifying barrel-like protease processed peptides according to the method described herein.

According to some embodiments of the invention, the contacting is effected on isolated barrel-like proteases according to some embodiments of the invention.

According to some embodiments of the invention, the contacting is effected on non-isolated barrel-like proteases.

According to some embodiments of the invention, the contacting is effected prior to and following the contacting, wherein a shift in profile of the barrel-like proteases-processed peptides is indicative of an effect of the test compound.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic representation of the 'Proteasome Profiling' system workflow. Cells are treated with peptidase inhibitors and cross-linkers, lysed and the proteasomes are immunoprecipitated using specific antibodies. The eluted immunocomplex is then separated on solid phase extraction into protein and peptide pools. Peptides are finally subjected to MS analysis;

FIG. 2 shows that purified proteasomes isolated according to some embodiments of the invention are catalytically active. Purified proteasome complexes were incubated in activity based assay mixtures with fluorescent LLVY peptides as indicated in the table.

FIGS. 3A-B show MS analysis of 'Proteasome Profiling'. (FIG. 3A) Proteasomes were immunoprecipitated from HeLa cells using anti-α6 antibodies. Peptides and proteins were eluted from the immune-complex using 30% and 80% acetonitrile (ACN), respectively. The following samples were separated on SDS-PAGE gel and stained with Coomasie Brilliant Blue Dye: total extract (input); Flow-through following precipitation of the immune-complex (F.T.); residual proteins that remains bound to the beads following elution (Beads+α6); Precipitated beads incubated with cell extract without antibodies (Beads-α6); Eluted peptides (30%); Eluted proteins (80%). (FIG. 3B) MS spectra of the eluted peptide fraction.

FIGS. 4A-C are graphs showing that peptides identified by proteasomal profiling exhibit unique and different properties than peptides generated by tryptic digest. MS analysis data of peptides isolated by 'Proteasome Profiling' was compared to data generated from peptides following tryptic digest according to number of charges (FIG. 4A), C-terminal amino acid composition (FIG. 4B), and peptide length (FIG. 4C).

FIGS. 5A-C show the significant enrichment in detection of extreme-abundance proteins compared to conventional MS analysis. (FIG. 5A) Abundance of identified proteins compared with a conventional reference MS of HeLa cells. (FIGS. 5A-B) Zoom-in on low abundance range less than 10 ppm (FIG. 5B) and high abundance range more than 500 ppm (FIG. 5C). Protein abundance was assessed by PaxDb server (Wang, M. et al. Proteomics 2015, Volume 15, Issue 18 3163-8), using measure of *H. sapiens*-Whole organism (Integrated).

FIGS. 6A-B show the advantageous detection of short-lived proteins compared to conventional MS. (FIG. 6A) Half-lives of detected proteins compared with a conventional reference MS of HeLa cells. (FIG. 6B) Zoom-in on short half-lives range less than 40 shows an advantage for the 'Proteasome Profiling' method. Protein half-lives values were assessed using a quantification by dynamic SILAC and LC-MS/MS of Sandoval et al (JASN November 2013 vol. 24 no. 11 1793-1805).

FIG. 7 shows the number of unique peptides which are evident following MS analysis of HEK293 cell lysate. The full treatment ("untreated"), depletion of the cross-linker (−DSP), depletion of cellular proteases (−TPP) or depletion of both the cross-linker and cellular proteases (−DSP−TPP). Of note, the addition of proteasome inhibitors such as Velcade (40 nM) or Epoxomycin (1 nM) significantly reduced the number of identified peptides, suggesting that the 'Proteasome Profiling' detects the peptides which are processed by the proteasome itself or at its vicinity.

DESCRIPTION OF SPECIFIC EMBODIMENTS
OF THE INVENTION

The present invention, in some embodiments thereof, relates to methods of isolating barrel-like proteases and identifying peptides processed thereby.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

All the peptides produced by the degradation of proteins in the cell are referred to as "Degradome". Similarly to the genome, transcriptome and proteome, the ability to accurately analyze the degradome in a dynamic manner is expected to shed light on a variety of cellular processes and to provide new insights which can be used in drug development, treatment and diagnostics.

Whilst reducing the present invention to practice, the present inventors have devised a system for identification of the 'active degradome' or in other words, the proteins that are actively degraded by barrel-like proteases in cells. The essence and major advantage of the present approach is the ability to "zoom-in" on cleaved peptides that are generated by the barrel-like proteases in cells, and therefore reflect the proteins that are being actively degraded and regulated in the cells, under specific conditions. Importantly, the present analysis is dependent on a novel workflow for processing the biological samples, which is different from current practices in the MS field. The ability to capture and analyze the endogenous peptides offers a novel way of identifying key regulators in various states of biological conditions such as stem cell differentiation, cancer, immune cell activation and inflammation, viral/bacterial infections, changes of the microbiome, response to therapy, aging and other clinical indications. Since the different conditions mentioned above are expected and known to alter the cellular program, it is expected that a different set of proteins will be targeted to degradation and therefore the present assay will identify changes of putative regulatory proteins, which may be expressed at low abundances, and are often masked by looking at whole-proteome samples.

Figure 1:
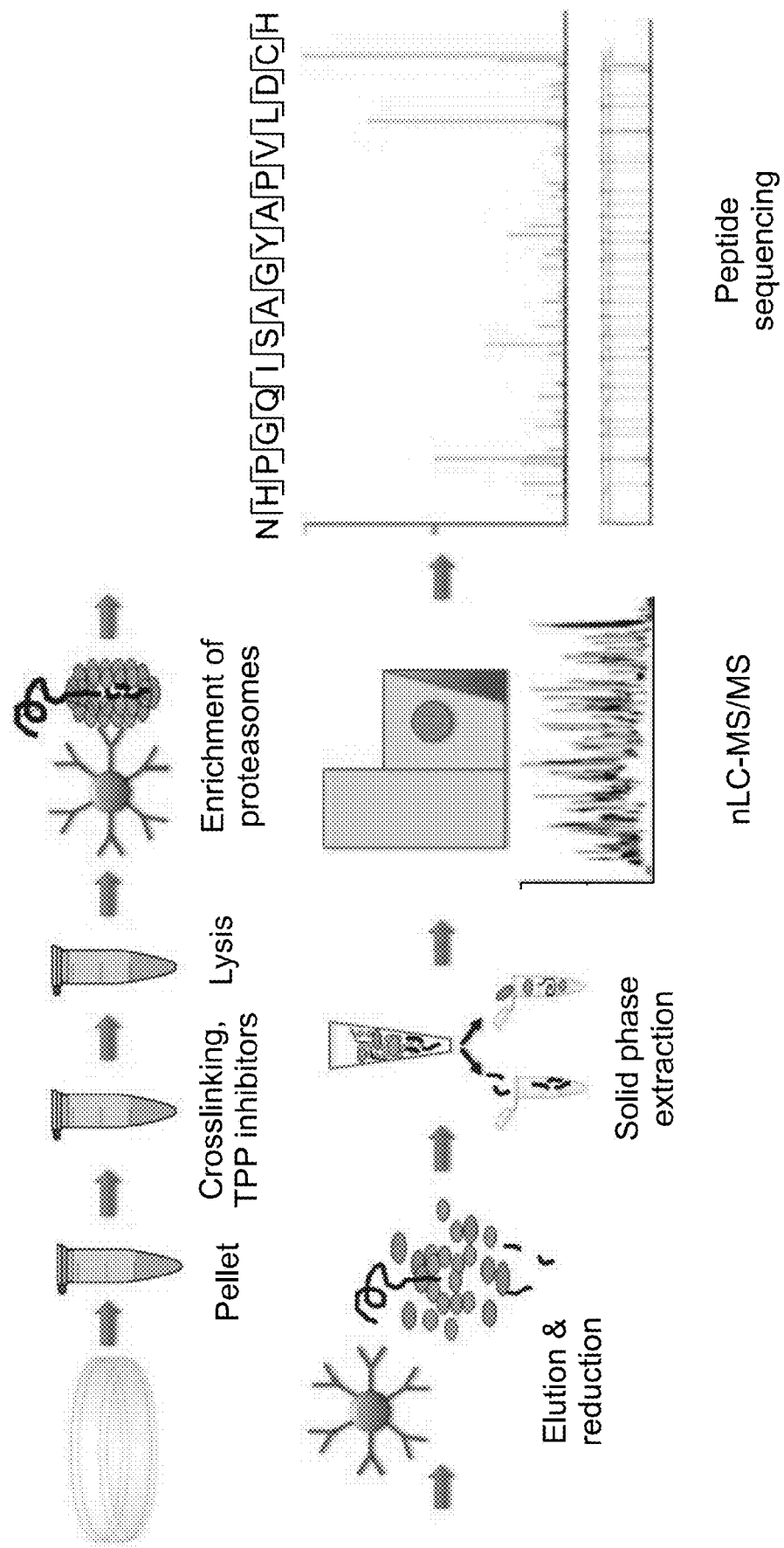
Figure 2:
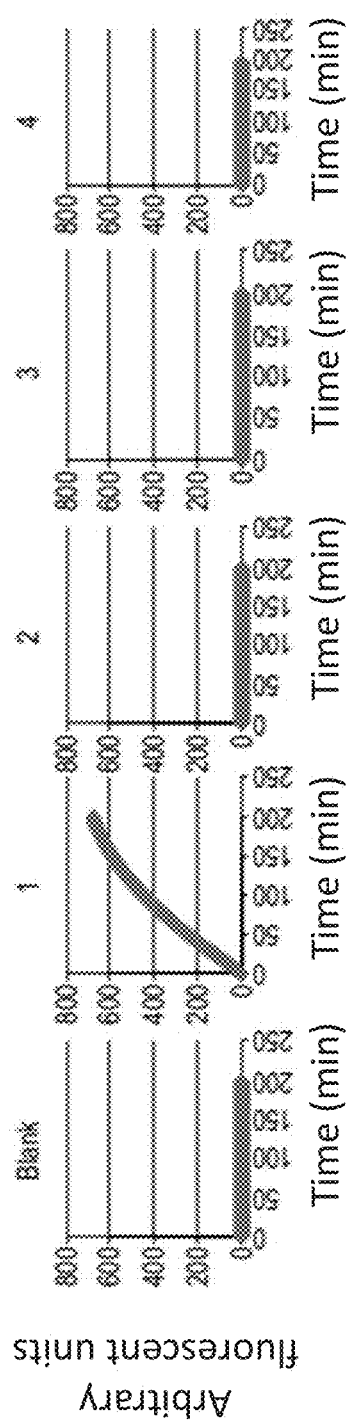

As is illustrated hereinbelow and in the Examples section which follows, a unique system of 'Proteasomal Profiling' was developed for the isolation the active-degradome from the cell. As will be readily understood by the skilled artisan, this work flow may be adapted to any barrel-like protease. Thus, the present assay is done by purifying the protease peptide pool, which represents proteins actively undergoing degradation at the time of experiment. An embodiment of the workflow of the assay is shown in FIG. 1. Proteasomal complexes are effectively purified by immunoprecipitation using specific antibodies against a proteasomal subunit or associated molecules e.g., α6 subunit of the 20S core particle. FIG. 2 shows that the catalytic activity of the proteasomes is retained during the purification procedure, as determined by an activity-based assay that was performed using a fluorescent peptide substrate. Example 2 shows that to stabilize the peptide pool within the proteasome, peptidases inhibitors are used to protect from degradation by peptidase upon exit from the proteasome, together with chemical cross-linkers that retain the generated peptides in the vicinity of the proteasome. Mass-spectrometry analysis established the successful isolation and characterization of the proteasome processed peptides.

Thus, according to an aspect of the invention there is provided a method of isolating barrel-like proteases. The method comprising isolating barrel-like proteases from a biological sample containing the barrel-like proteases under conditions that maintain the content of the barrel-like protease-processed peptides in the barrel-like proteases upon the isolation, thereby isolating the barrel-like proteases.

As used herein the phrase "barrel-like protease" refers to a protease having a degradation chamber formed by a monosubunit or a multisubunit (e.g., 2, 3, 4 or more) barrel-shaped/fold or cavity/chamber/pocket/groove/cleft or capturing-peptide complex. The barrel-like is a structural fold, usually consists of beta-barrels. According to a specific embodiment, the barrel-like domains in proteases are typically comprised in globular proteins, having two sub-domains of the beta barrel fold (dimer). For example, a two domains topology exists in the pepsin-like family, fold number (50646) in SCOP database for structural classification of proteins. Another example is the Trypsin-like serine proteases [fold number 50493], and in the Trypsin-type beta(6)-barrel (fold 2000083).

According to a specific embodiment, the barrel-like protease is a soluble protein.

According to a specific embodiment, the barrel-like protease is a membrane-bound protein.

According to a specific embodiment, the barrel-like protease can be from any organism, be it eukaryotic (mammalian, e.g., human, animal, plant (e.g., monocot or dicot, whole plant or parts/cells thereof, higher plant or lower plant), yeast, algae) or prokaryotic.

Examples of barrel-like proteases include, but are not limited to ATP-dependent barrel like proteases.

Examples of barrel-like proteases include, but are not limited to Clpxp, clpP, immunoglobulin A1 proteases, HsIV peptidase and VCP/p97.

Other examples are listed infra:

A. Barrel-like protease families which include HUMAN proteins. Interpro family IDs are noted in parenthesis.

Family: Peptidase C1A, cathepsin K (IPR015644) Family: Cathepsin 3 (IPR015645) (mouse)

Domain: Peptidase C12, ubiquitin carboxyl-terminal hydrolase (IPRO01578)

Aspartic peptidase A1 family (IPR001461):
BACE2 is a membrane-bound aspartic protease of the A1 family (www(dot)ncbi(dot)nlm(dot)nih(dot)gov/pubmed/16305800)
cathepsin D
kallikreins: a subgroup of the chymotrypsin-like serine proteinase family S1A of clan PA(S). i.e Human Epidermal Kallikrein 7 (hK7)

B. Barrel-like protease families including prokaryotic and other eukaryotic species. For example:

Beta-barrel assembly-enhancing protease (BepA) (IPR030873)
Peptidase A25
Serine endopeptidase DegP2 (IPRO15724)
Peptidase C10, streptopain (IPR000200)
Peptidase C11, Clostripain Clostridium species (IPR014173)
Hepatitis E virus, cysteine peptidase (IPR008748)

C. Barrel-like protease families in plants, bacteria, and more:

D. Family of Peptidase A25, germination protease-mostly in bacteria

E. Family Peptidase S1C: in plants (rice), zebrafish, human, mouse, etc.

Peptidase A5, thermopsin-mostly in archaea

Aspartic peptidase A1 family—in rice, fruit fly, mouse, human, etc.

According to a specific embodiment, the barrel-like protease is a proteasome (e.g., human proteasome).

As used herein the term "proteasome" refers to protein complexes inside all eukaryotes and archaea, and in some bacteria. The main function of the proteasome is within the ubiquitin-mediated degradation system in which the proteasome is the key catalytic unit, which in addition to regulating various cellular processes also plays a critical role in the regulation of the immune system by generating the majority of the major histocompatibility complex (MHC) class I precursor peptides from both autologous and foreign proteins.

According to embodiments of the invention, the proteasome complex is a 670 kDa 26S barrel-shape (i.e., barrel-like) structure comprising a catalytic 20S core and two 19S regulatory complexes. The 20S core consists of four rings, containing seven proteins in each ring. The two outer rings are composed of 7 alpha subunits ($\alpha1$-$\alpha7$) and the two inner rings are composed of 7 beta subunits ($\beta1$-$\beta7$). Attached to the alpha subunit rings is a 6-subunit ring constituting the base, to which is attached a 9-subunit ring lid. The base and lid together constitute the 19S regulatory complex.

As used herein a protein associated with a barrel-like protease refers to any molecule e.g., protein which interacts with the barrel-like protease and co-immunoprecipitates therewith in the presence or absence of a cross-linking agent as described below.

According to a specific embodiment, the proteasome is a constitutive proteasome. Accordingly, the active centers are located within the beta subunits of the barrel complex: $\beta1$ (caspase-like activity), $\beta2$ (trypsin-like activity) and $\beta5$ (chymotrypsin-like activity).

According to a specific embodiment, the proteasome is an immunoproteasome, which is typically formed during stress or infection, or following stimulation with pro-inflammatory cytokines, interferon gamma and/or tumor necrosis alpha or lipopolysaccharide. In immunoproteasomes $\beta1i$ (LMP2), $\beta2i$ (MECL1) and $\beta5i$ (LMP7) are incorporated into the nascent proteasomes thereby replacing their constitutive homologs, the $\beta1$, $\beta2$ and $\beta5$ subunits. In addition a 6-subunit PA28$\alpha\beta$ complex replaces the 19S regulatory complex As used herein the term "isolating" refers to isolation from the natural environment, i.e., the cells, exosomes, microparticles or the serum, in case of circulating cell-free barrel-like proteases (e.g., proteasomes).

According to a specific embodiment, upon isolation the barrel-like proteases (e.g., proteasomes) are substantially active (e.g. catalytically active).

According to a specific embodiment, upon isolation the barrel-like proteases (e.g., proteasomes) are substantially inactive.

The functional activity of barrel-like proteases (e.g., proteasomes) is determined by their enzymatic activity. Such assays are typically done using a fluorogenic substrate. For instance in the case of proteasomes, the following substrates can be used: Chymotrypsin substrate: Suc-LLVY-AMC, Trypsin substrate Ac-RLR-AMC or Caspase substrate Z-LLE-AMC, all available from Enzo-life Sciences.

As used herein the phrase "biological sample" refers to an ex-vivo or in-vitro sample which comprises the cell-free- or cell-associated barrel-like protease of interest e.g., proteasome.

According to a specific embodiment, the barrel-like proteases are derived from a healthy tissue or cell.

According to a specific embodiment, the barrel-like proteases are derived from a pathogenic tissue or cell.

Examples of biological samples which can be used in accordance with the present teachings include, but are not limited to intact cells in suspension, tissue biopsy, cell-free proteasomes, exosomes or microparticles which may be derived e.g., body fluids such as whole blood, serum, plasma, cerebrospinal fluid, urine, lymph fluids, and various external secretions of the respiratory, intestinal and genitourinary tracts, tears, saliva, milk; as well as white blood cells, malignant tissues, senescent tissues or cells, peritoneal lavage, amniotic fluid and chorionic villi.

Alternatively, the biological sample is a cell/tissue culture of primary cells or cell lines or alternatively, of any microorganism (e.g., yeast, bacteria, fungi) that comprises barrel-like proteases.

According to a specific embodiment, the biological sample does not comprise immune cells.

According to a specific embodiment, the biological sample comprises immune cells (e.g., activated or non-activated).

According to a specific embodiment, the immune cells are antigen presenting cells which may be "professional" antigen presenting cells e.g., human CD4+ T cells, B cells, macrophages and dendritic cells (e.g. derived from peripheral blood mononuclear cells) or non-professional antigen presenting cells. Non-professional antigen presenting cells include all nucleated cell types in the body. They use an MHC class I molecule coupled to beta-2 microglobulin to display endogenous peptides on the cell membrane. These peptides originate within the cell itself, in contrast to the exogenous antigen displayed by professional APCs using MHC class II molecules. Cytotoxic T cells are able to interact with endogenous antigen presented using an MHC class I molecule.

According to a specific embodiment, the immune cells are activated immune cells.

According to a specific embodiment, the immune cells are naive immune cells.

According to a specific embodiment, the biological sample comprises cancer cells.

According to a specific embodiment, the biological sample comprises pathogen-infected cells.

According to a specific embodiment, the biological sample comprises stem cells or progenitor cells.

As used herein, the phrase "stem cells" refers to cells, which are capable of remaining in an undifferentiated state (e.g., pluripotent or multipotent stem cells) for extended periods of time in culture until induced to differentiate into other cell types having a particular, specialized function (e.g., fully differentiated cells). Preferably, the phrase "stem cells" encompasses embryonic stem cells (ESCs), induced pluripotent stem cells (iPS), adult stem cells, cancer stem cells, mesenchymal stem/stromal cells and hematopoietic stem cells.

According to a specific embodiment, the biological sample comprises senescent cells.

Typically, senescent cells no longer replicate, they remain metabolically active and commonly adopt an immunogenic phenotype consisting of a pro-inflammatory secretome, the up-regulation of immune ligands, a pro-survival response, promiscuous gene expression (pGE) and stain positive for senescence-associated β-galactosidase activity. The nucleus of senescent cells is characterized by senescence-associated heterochromatin foci (SAHF) and DNA segments with chromatin alterations reinforcing senescence (DNA-SCARS).

Regardless of the tissue, cell or culture employed, the sample is typically (but not necessarily) subjected to fractionation. That is, the phase containing the majority of the barrel-like protease of interest may be isolated. Thus, if the barrel-like protease is comprised in the cells, then the sample is subjected to centrifugational conditions that precipitate the cells and the pellet is collected. Other conditions will apply when the protease of interest is comprised in exosomes, particles, specific organelles, cell membranes and the like. The skilled artisan will know which method of isolation to select.

The sample is subject to treatment with peptidase inhibitors, which should maintain the peptide pool intact even after cell lysis for instance.

As used herein "maintaining an intact peptide pool" refers to the peptides processed (produced) by the barrel-like protease of interest. Accordingly, this is achieved by eliminating peptidase activity, an activity that further degrades the products of the barrel-like protease; and maintaining the barrel-like protease processed peptides in the vicinity of the barrel-like protease, such that the barrel-like protease and products thereof are co-isolated.

As used herein "peptides" refer to the peptides which are produced by i.e., direct degradation products of the barrel-protease of interest, also referred to as barrel-like protease processed peptides.

Thus in the case of a proteasome, the peptides are typically 2-25 amino acids in length. Proteasomes typically cleave at the hydrophopic, aromatic and basic amino acids of proteins. The enzymatic activity and the generated repertoire have been shown to be cell type and immune organ-specific.

As used herein "peptidase" also termed proteases, proteinases and proteolytic enzymes, refers to a hydrolase which acts on peptide bonds, E.C. 3.4.

Examples include, but are not limited to:
3.4.11: Aminopeptidases
3.4.12: Peptidylamino-Acid Hydrolases or Acylamino-Acid Hydrolases
3.4.13: Dipeptidases
3.4.14: Dipeptidyl-peptidases and tripeptidyl-peptidases
3.4.15: Peptidyl-dipeptidases
3.4.16: Serine-type carboxypeptidases
3.4.17: Metallocarboxypeptidases
3.4.18: Cysteine-type carboxypeptidases
3.4.19: Omega peptidases
3.4.21: Serine endopeptidases
3.4.22: Cysteine endopeptidases
3.4.23: Aspartic endopeptidases
3.4.24: Metalloendopeptidases
3.4.25: Threonine endopeptidases
3.4.99: Endopeptidases of unknown catalytic mechanism As used herein "a peptidase inhibitor" refers to molecules that inhibit the function of peptidases. Many naturally occurring protease inhibitors are proteins. Examples include, but are not limited to:

Serine proteases: PMSF, PMSF plus, DFP, Pefabloc SC, Pefabloc SC Plus, antithrombin III, aprotinin, 3,4-Dischloroisocoumarin, leupeptin (inhibits serine and cysteine proteases with trypsin-like specificity);

Cysteine proteases: E-64;

Metalloproteases: EDTA-Na2; phosphoramidon; bestatin (aminopeptidases), TIMP-2 (matrix metalloprotease);

Aspartic proteases: pepstatin.

Calcium-dependent proteases—EGTA;

A non-binding list of protease specific inhibitors is provided infra.

Antipain dihydrochloride—for the inhibition of Papain, Trypsin (Plasmin);

Calpain Inhibitor I—for the inhibition of Calpain I>Calpain II;

Calpain Inhibitor II—for the inhibition of Calpain II>Calpain I;

Chymostatin—for the inhibition of Chymotrypsin;

Hirudin—for the inhibition of Thrombin;

TLCK.HCl—for the inhibition of trypsin, other serine and cysteine proteases (e.g., Bromelain, Ficin, Papain);

TPCK—for the inhibition of Chymotrypsin, other serine and cysteine proteases (e.g., Bromelain, Ficin, Papain);

α2-macroglobulin-general endoproteinase inhibitor;

Phosphoramidon-specifically inhibits thermolysin, collagenase, and metalloproteases TIMP2-inhibits matrix metalloproteases;

Trypsin-Inhibitor (chicken egg white, soybean)—for the inhibition of Trypsin.

To achieve maximal inhibition of proteases in the sample, protease inhibitor cocktails are generally used.

Protease inhibitors and cocktails thereof are available from various manufacturers e.g., Roche Molecular Biochemicals. The effective concentration for inhibition is known to the skilled artisan of per manufacturer's instructions (see e.g., the Examples section which follows).

As mentioned, the conditions for maintaining the content of the barrel-like protease processed peptides include maintaining the barrel-like protease processed peptides in the vicinity of the barrel-like protease, such that the barrel-like protease and products thereof are co-isolated.

To achieve that, the conditions comprise the use of a cross-linking agent.

As used herein "a cross-linking agent" refers to a molecule or physical condition (e.g., irradiation) that forms a chemical reaction that forms cross-links.

A non-limiting list of cross-linkers that can be used in accordance with the present teachings include, but are not limited to, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, cleavable cross-linkers dithiobis(sulfosuccinimidylpropionate), DTS SP, SMCC or Sulfo-SMCC, DST, BSOCOES, EGS, DTBP, DST, DTME, LC-SPDP, SMPT, SPDP, SMCC and MBS.

The selection of the specific cross-linking agent depends on the distance of the barrel-like protease processed peptides from the catalytic site of the barrel-like protease and on the functional groups.

Following treatment under the above conditions, the sample is subjected to cell lysis when needed.

A variety of conditions are known to effect cell lysis. The skilled artisan will know which method to select based on the biochemical (e.g., soluble, non-soluble) and cellular (e.g., cellular localization) properties of the barrel-like protease. During cell lysis, protease inhibitors are still present in the solution. According to one embodiment all steps are effected at 4° C. (e.g., on ice) to achieve maximal inhibition of protease activity.

Isolation or enrichment (see for example FIG. 1) of the barrel-like protease is typically achieved by immunological methods e.g., immunoprecipitation, to achieve maximal enrichment of the specific barrel-like protease and its processed peptides.

The method enables the purification of a protein or any target molecule for which antibodies can be obtained. For instance, an antibody to the protein of interest is incubated with a cell lysate (or any biological sample as described herein) enabling the antibody to bind to the target in solution. The antibody/antigen complex is then pulled out of the sample using a solid phase e.g., agarose beads/magnetic beads to which an affinity moiety for the antibody used is coupled. Alternatively or additionally, the antibody to the target is directly bound to the solid phase.

Thus, immunoprecipitation may use an antibody to the barrel-like protease i.e., any of its subunits.

Alternatively or additionally, immunoprecipitation employs an antibody that is directed to an auxiliary target (e.g., protein, small molecule, post-translational modification and the like) that will co-precipitate the barrel-like protease.

Such an auxiliary target may be a protein that associates with the barrel-like protease or is in sufficient vicinity to be cross-linked with the barrel-like protease.

The auxiliary target me be endogenous to the biological sample or may be exogenously added.

Measures are taken to choose an antibody that binds its target antigen even following cross-linking, in most cases in a denatured form.

Accordingly, in the case of the proteasome, immunoprecipitation can be done using an antibody to either proteasome subunits, but also other specific associated proteins such as E3 ligases, deubiquitinating enzymes, non-degradable forms of ubiquitin poly-chains, PA28-20S proteasome activator, and small molecule inhibitors or mutant forms of proteins which will be bound specifically to the proteasome and may provide a "bait".

Specific targets that can be used to pull-down the proteasome are described in www(dot)jcsdotbiologists(dot)org/content/122/14/2325(dot)full; www(dot)molbiolcell(dot)org/content/early/2007/12/27/mbc(dot)E07-10-1040(dot)fulldotpdf); and PA28 www(dot)jbcdotorg/content/269/50/31466(dot)full(dot)pdf, each of which is incorporated herein by reference in its entirety.

According to a specific embodiment, the proteasome is precipitated using an antibody to any of the following targets: PSMC2, PSMC1, PSMC4, PSMC6, PSMC5, PSMD1, PSMD3, PSMD12, PSMD11, PSMD6, PSMD7, PSMD17, PSMD4, PSMD14, PSMD10, ADRM1, WDR71, SHFM1, PSMA6, PSMA2, PSMA4, PSMA7, PSMA5, PSMA1, PSMA3, PSMB6, PSMB7, PSMB3, PSMB2, PSMB5, PSMB1, PSMB4, SPME1, SPME3, SPME2, SPME4, USHL5, UBE31, UBC, RAD23B, UBQLN1, PSMA8, PSMB10, PSMB8, PSMB9, PSMC3, PSMD13, PSMD2, PSMD5, PSMD8, PSMD9, PSME1, PSME2, PSME3, PSME4 or PSMF1. Antibodies to these targets are commercially available e.g., from Cell Signaling Technologies, Enzo Life Sciences, Santa Cruz Biotechnology or Abnova Corporation).

According to a specific embodiment, the proteasome is precipitated using an antibody targeting LMP2 (e.g. for precipitation of an immunoproteasome).

According to a specific embodiment, the proteasome is precipitated using an antibody targeting α6 subunit (e.g. for precipitation of constitutive-proteasomes (cP)). According to one embodiment, the proteasome is precipitated using any protein purification method known in the art, such as but not limited to, fractionation, affinity chromatography (e.g. using a protein tag fused and expressed together with the proteasome, e.g. HA-, His-, Flag-tags), aptamer-based affinity purification, chemical pull-down with e.g. glutathione-, metal chelate (cobalt or nickel)- or biotin-coated agarose beads used to capture glutathione S-transferase (GST)-, polyHis- or streptavidin-tagged protein or binding domains, respectively.

It will be appreciated that isolation or enrichment of the barrel-like protease of the invention may be carried out using any protein purification method capable of purifying components of the proteasome or any proteasome associated protein or proteasome binder protein (e.g. ubiquitin).

The present teachings have been exemplified on proteasome isolation as shown in Example 1.

Examples for cleavage site/substrate specificity of HUMAN proteases:

1. cathepsin K protease degrades collagen fibers (Aguda, 2014 vol. 111 no. 4917474-17479, doi: 10.1073/pnas.1414126111)

2. Clp in human mitochondria exhibit preferences for certain amino acids in the P1, P2, and P3 positions: Gersch et al. *ACS Chem. Biol.*, 2016, 11 (2), pp 389-399.

3. BACE2 is a membrane-bound aspartic protease of the A1 family with a high level of sequence homology to BACE1. cleaving Aβ-peptides from the amyloid precursor: Ostermann et al. J. Mol. Biol. Volume 355, Issue 2, 13 Jan. 2006, Pages 249-261

4. Human Epidermal Kallikrein 7 (hK7): hK3/PSA and hK7 exhibited a chymotrypsin-like specificity preferring large hydrophobic or polar residues at the P1 position (Debela et al. 2006 Journal of Biological Chemistry, 281, 25678-25688.)

5. Non-human IgA1 proteases: specifically cleave the peptide bond distal to the second proline (shown by the vertical line) in the sequence P-P-I-T-P, P-S-P-I-S, or P-T-P-I-S-P. (Vitovski et al. Infect. Immun. June 2007 vol. 75 no. 6 2875-2885)

Accordingly, there is provided a barrel-like protease e.g., proteasome, preparation obtainable according to the teachings described herein.

The majority of proteins (high molecular e.g., above 100 amino acids, 50 amino acids or 30 amino acids) in the preparation is the barrel-like protease and associated targets which are cross-linked to the barrel-like protease. The preparation further comprises the barrel-like protease processed peptides also in a cross linked manner. Although the preparation may be subjected to conditions e.g., reducing conditions, that remove or reverse the cross-links. According to a specific embodiment, the preparation further includes at least one type of a cross-linking agent e.g., as described herein. The preparation is essentially devoid of most abundant cellular proteins e.g., in plant cells-rubisco; in bacterial cells—ribosomal proteins and their ancillary components, acyl carrier protein, elongation factor EF-TU, Rp1L, FimA, LacZ; in yeast-cell wall protein (YKL096W-a), the Plasma membrane H+-ATPase (YGLOO8C), and Fructose 1,6-bisphosphate aldolase (YKL060C); in mammalian cells—Actin, Histone H4, HistoneH2A 1-F, HistoneH2B 2-B, Histone H3.2, EEF1A1, RPS27A, Protein S100-A4, Annexin A2 and TUBBS.

The preparation may comprise the cross-linking agent and the peptidase inhibitors.

Once the barrel-like protease preparation is at hand, the peptide pool is isolated from total proteinaceous pool of the isolated barrel-like proteases.

Thus, according to an aspect of the invention there is provided a method of isolating barrel-like protease-processed peptides, the method comprising:
(a) isolating barrel-like proteases; and
(b) isolating a peptide pool from total proteinaceous pool of the isolated barrel-like proteases, thereby isolating the barrel-like protease-processed peptides.

The peptides are eluted from the barrel-like protease using reducing/denaturing/cleaving/deconjugating agents which may be used for elution mostly concomitant with or followed by reduction (to elute the cross-linked peptides). An exemplary protocol which should be understood as no limiting since there is a myriad of protocols for eluting the peptides is: 50 mM DTT, 37 Celsius for 30 minutes with shaking.

According to a specific embodiment, isolating the peptide pool from total proteinaceous pool of the isolated barrel-like protease is effected by solvent precipitation followed by solid phase extraction.

Hydrophilic peptides for instance are generally extracted using solutions of organic acids whereas organic solvents are used to obtain highly hydrophobic peptides.

The selectivity of precipitation directly depends on the type of precipitating agent applied. In addition to the use of organic solvents such as ethanol, methanol, acetonytril (acetonitrile), acetone or any organic solvent, solutions containing acids such as TCA or tri fluoroacetic acid (TFA) or acetic acid are classical protein precipitants. Salting out precipitation, based on polarity, with high concentrations of salts or precipitation by adjusting the pH to the pI of protein are other options.

Ultracentrifugation/Density gradient/Osmolarity/Isoelectric focusing

Ultrafiltration

Ultrafiltration is mainly useful for fractionating peptides as well as the removal of proteins and other macromolecules based on their molecular size. A recent technology named electrodialysis with ultrafiltration membranes (EDUF) has been developed to fractionate peptides from complex mixtures on the basis of their electrical charge, size, or molecular weight. A conventional electrodialysis is used but some ion exchange membranes are replaced by ultrafiltration ones.

Liquid Chromatography

Size exclusion chromatography (SEC) fractionates peptides on the basis of their molecular size. This technique separates analytes through a bed of porous beads where they can either enter or be excluded from the internal space of the beads based on their size. Elution occurs from the largest to the smallest analyte over time. Several resins with different pore sizes are commercially available. Cross-linked dextran (Sephadex) resins are mostly used but polyacrylamide (Bio-Gel P) or divinylbenzene polymers are also available as stationary phases. Depending on the resin composition, peptides are eluted with water, organic acids, ammonia, or ammonium salts, even as alcoholic solutions that reduce potential hydrophobic interactions.

Ion exchange chromatography (IEX) constitutes another technique for peptide fractionation. In this case, peptides are fractionated according to their net surface charge/polarity. Porous or nonporous matrices with hydrophilic materials such as cellulose, cross-linked dextrans, polystyrene polymers (Dowex resins), or Bio-Rex membranes are very useful as anion or cation exchange stationary phases. These matrices are substituted with functional groups that determine the charge of the medium (e.g., quaternary ammonium, diethylaminoethyl, sulfopropyl, carboxymethyl, etc.). Measures are taken not to increase the ionic strength to be compatible with techniques such as MS.

Solid-Phase Extraction

Solid-phase extraction (SPE) is based on the same principle of affinity-based separation as liquid chromatography. SPE enables retention and elution of analytes from complex mixtures, removal of interfering compounds, and sample concentration.

SPE is available in normal phase, reverse-phase, and ion exchange modes, reversed phase being one of the most used formats. Based on the wide range of physicochemical properties of the analytes, several commercial sorbents (e.g., C18, C8, C2, phenyl, cyanopropyl, and ion exchange bonded materials, among others) are supplied to improve the versatility of SPE.

Peptide derivatization may be necessary in some analyses for better detection. Most derivatizations are developed with fluorescent labels to become detectable with fluorescence detection whose limit of detections (LODs) is about 2-3 orders of magnitude lower than common UV-absorption detections.

The peptide preparation obtainable following isolation from the barrel-like (e.g., protease) preparation is characterized by a profile characteristic of the activity of the isolated barrel-like protease e.g., constitutive proteasome, immune proteasome or both. As mentioned, the peptide repertoire characteristic of proteasome activity is of peptides 2-25 amino acids in length. Proteasomes typically cleave at the hydrophopic, aromatic and basic amino acids of proteins.

The enzymatic activity and the generated repertoire have been shown to be cell type and immune organ-specific.

This preparation is now subject to sequence analysis.

Thus according to an aspect of the invention, there is provided a method of identifying barrel-like protease-processed peptides, the method comprising:

(a) isolating the barrel-like protease-processed peptides as described above; and (b) subjecting the barrel-like protease-processed peptides to sequence analysis, thereby identifying the barrel-like protease-processed peptides.

According to a specific embodiment, the sequence analysis is effected by mass-spectrometry (MS).

According to a specific embodiment, the preparatory phase and sequencing comprises liquid chromatography mass-spectrometry (LC-MS).

The present teachings are highly useful in gaining insight for various biological processes.

Thus, according to an aspect of the invention there is provided a method of testing an effect of a test compound or condition, the method comprising:

(a) contacting a biological sample comprising barrel-like proteases with the test compound; and subsequently (b) identifying barrel-like protease processed peptides.

As used herein, the term "test agent" refers to a molecule(s) or a condition.

Examples of molecules which can be utilized as agents according to the present invention include, but are not limited to, nucleic acids, e.g., polynucleotides, ribozymes, microRNAs, siRNAs and antisense molecules (including without limitation RNA, DNA, RNA/DNA hybrids, peptide nucleic acids, and polynucleotide analogs having altered backbone and/or bass structures or other chemical modifications); In this case, the nucleic acid agents are either contacted as naked DNA/RNA with the cells or form a part of a nucleic acid expression construct or library which are used along with transformation/transfection or infection protocols.

Other examples of molecules which can be utilized as agents according to the present invention include, but are not limited to a biomolecule e.g., a metabolite, a protein, a lipid, a carbohydrate, a nucleic acid (as described above) or a combination of same; and "small molecule" drug candidates. "Small molecules" can be, for example, naturally occurring compounds (e.g., compounds derived from plant extracts, microbial broths, and the like) or synthetic organic or organometallic compounds having molecular weights of less than about 10,000 daltons, preferably less than about 5,000 daltons, and most preferably less than about 1,500 daltons.

Examples of conditions suitable for use as agents according to the present invention include, but are not limited to culturing conditions, such as, for example, temperature, humidity, atmospheric pressure, gas concentrations, growth media, contact surfaces, and the presence or absence of other cells in a culture.

Thus, depending on the agent, contacting may be effected at various stages of the procedure.

Thus according to a specific embodiment, contacting with the test agent is effected on isolated barrel-like proteases.

Alternatively, contacting is effected on non-isolated barrel-like proteases.

According to an embodiment of the invention, contacting is effected prior to and following the contacting, wherein a shift in profile of the barrel-like proteases-processed peptides is indicative of an effect of the test compound.

Thus, the present methods and preparations stemming therefrom can be used in various proteomic studies of various biological systems. The fact that the present teachings rely on the use of standard resources make it highly available for wide use for various purposes some of which are detailed below for proteasomes.

Cancer

Proteasomes are often upregulated in transformed cells as a mechanism to cope with large quantities of misfolded or aberrantly overexpressed proteins. Interestingly, cancer cells depend on the proteasomal activity for survival and several proteasome-inhibitors are in clinical use or trials as anti-cancer therapies. Application of the present teachings e.g., identifying the proteasome processed peptides from biopsies taken from different malignancies can lead to the identification of an individual "fingerprint" of each cancer, depicting principal activated processes. Moreover, increased degradation of specific proteins is beneficial for the tumorigenic properties of the cell. Therefore, identification of such proteins provides insightful information for the understanding of the altered molecular pathways that underlie that transformation event. Proteomic changes that are often missed in conventional analyses, such as that of low abundance or rapid turned-over proteins, can be detected using the present teachings. It is suggested that the present peptide profiling analysis complements the conventional assays of gene-expression and immunohistochemistry and should provide a novel dimension in clinical diagnosis and in research.

An additional cancer-related application of the present teachings is in pre-clinical investigation of drug sensitivity of cancer cells. Acquisition of drug resistance is a major hurdle in anti-cancer treatments. It is envisaged that characterization of the 'active degradome' of different cancer-cell populations treated with different agents, according to the present teachings, would be a sensitive method of detection of proteomic changes. Identification of specific proteins that are differentially targeted for degradation or antigen processing in drug resistant versus sensitive cells, is beneficial for selecting or modifying treatments, and thus holds great therapeutic potential.

Immune System:

An intriguing application of the present teachings is in the profiling of immunoproteasomes. Under inflammatory conditions, cytokine-induced distinct subtypes of proteasomal beta subunits ($\beta 1i$, $\beta 2i$, and $\beta 5i$) are synthesized de novo, and are incorporated into newly assembled proteasomes, replacing the constitutive beta subunits. This results in the replacement of constitutive 20S proteasomes with immunoproteasomes, which have different cleavage specificities. Immunoproteasomes are responsible for antigen presentation and have an important role in defining the immune response. It is thus of significance to characterize the 'active degradome' of cells upon inflammation by profiling of immunoproteasomes. To isolate immunoproteasomes, antibodies against their distinct beta subunits (i.e. $\beta 1i$, $\beta 2i$, and $\beta 5i$) are used for the immunoprecipitation, following the same protocol described above. 'Thus applying the present teachings to immunoproteasomes to professional antigen-presenting cells, such as T cells, B cells, dendritic cells and macrophages, following viral or bacterial infection, can be used to identify an infection-induced 'active-degradome' signature. Using this method it is possible identify all peptides generated by the immunoproteasomes. This pool of peptides can then be classified into those targeted for surface presentation (using defined motifs) and those that have MHC-independent functions. The identification of the specific peptides generated by the immunoproteasomes, compared to peptides generated by constitutive proteasomes, of pathogen-infected versus normal cells is informative in understating host-pathogen responses. It also allows mapping of pathogenic proteins that are targeted for either antigen presentation or other cellular functions; and also of host proteins that are affected by the infection and processed by the proteasomes. Characterization of both is of major significance and holds therapeutic potential in understanding susceptibility to infection and proteomic changes that underlie compromised immune responses. In addition, it may be used in generating a novel type of 'molecular profile' which serves for evaluation of patient's response to drugs such as current immune checkpoint modulators or other targeted therapies or chemotherapeutic agents.

Other Pathologies:

Both proteasomes and immunoproteasomes have been implicated in various pathologies including diabetes, heart disease and neurodegenerative diseases. Therefore, application of 'Proteasome Profiling' to cells from each of these pathological conditions is beneficial to characterization of proteomic alterations in these cells. Of note, other than from tissues, proteasomes can be isolated from physiological fluids for this application. Circulating proteasomes have been demonstrated in the blood as well as in cerebrospinal fluid and there is a positive correlation between the concentration of serum circulating-proteasomes and the progression of pathologies such as hematologic malignancies, advanced stage metastatic malignant melanoma and various solid tumors, hepatic diseases, trauma patients and various auto-immune diseases. Therefore, isolation of proteasomes is accessible from different sources and 'Proteasome Profiling' provides an obtainable tool for analyzing different pathologies.

Stem Cell Reprogramming:

Reprogramming of stem cells is an extensively studied subject that presents great interest both to cell biologists as well as clinicians. Identifying critical events that take place en route to a reprogrammed state is of significance. Moreover, understanding cell behavior of iPS cells following induced differentiation is essential for successful generation of cells for therapy. Despite extensive study, there are still many open questions in the field, including: which cells of the population will reprogram, what proteomic changes occur in the first stage after induced-differentiation, what factors effect reprogramming rate and efficiency, and more. It is suggested that the present teachings can be used to characterize the yet undefined 'active degradome' of stem cell in different stages of differentiation. De-differentiation and reprogramming and may enhance significantly understating of these processes.

Data collected in such screens, particularly when tied to any clinical progression to conditions, will be of value in research and clinic. Such data arrays or collections can be stored in machine-readable media. Such computer storage media or device include ROM or magnetic diskette or others. Various systems can access the data directly from internal data storage or remotely from one or more data storage sites.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Experimental Procedures

Cell Lines and Antibodies.

293 and HELA cells were maintained in DMEM culture medium. Mouse hybridoma against PSMA1 (alpha 6 subunit) was reported in Proc Natl Acad Sci USA. 1990 September; 87(18):7071-5.

Purification of Proteasome Complexes.

Cells were treated with TPP inhibitors (100 mM PMSF (SIGMA), 2 Mm 1,10 phenanthroline (SIGMA)) for 5 min at 37° C. and incubated with the reversible cross-linker DSP (0.5 mM) for 30 minutes at 25° C. DSP was then quenched by the addition of L-cysteine (5 mM in 20 mM TRIS 7.4) for 10 minutes. Following PBS washes, the cells were lysed (0.25 mM HEPES pH 7.4, 10% glycerol, 5 mM $MgCl_2$, 1 mm ATP, Protease Inhibitors Mixture (Calbiochem)) for 30 minutes at 4° C., homogenized by freeze-thawing and passaged through a needle. Clear lysates were incubated with anti-α6 antibodies (100 μg of antibodies per 500-1000 μg of cell extract) for 18 hours at 4° C. before addition of Protein-G beads for 2 hours. Immunocomplexes were sequentially washed with ten volumes of NaCl (150 mM)+Tris.HCl (20 mM), ten volumes of NaCl (400 mM)+Tris.HCl (20 mM), ten volumes of NaCl (150 mM)+Tris.HCl (20 mM), and finally with seven volumes of Tris.HCl (20 mM), all at pH 8. The precipitated complex was eluted by DTT (50 mM) followed by acetic acid (0.1 N). Small aliquots of each elution fraction were analyzed by 12% SDS-PAGE to evaluate the yield and purity of the eluted proteasome peptides.

Purification and Concentration of Proteasome Peptides.

Eluted proteins and peptides were loaded on Micro tip-coulmn C-18 cartridges (Harvard Apparatus, Holliston, Mass.) that were prewashed with 80% acetonitrile (ACN) in 0.1% trifluoroacetic acid (TFA) and 0.1% TFA only. Following loading, the cartridges were washed with 0.1% TFA. Peptides were separated from proteins by elution with 30% ACN in 0.1% TFA and further purified on an Ultra-Micro Tipcoulm C-18 cartridge by elution with 80% ACN in 0.1% TFA. The peptides were concentrated using vacuum centrifugation.

Proteasome Activity-Based Assay.

Purified proteasomes were incubated with the fluorogenic substrate peptide Suc-LLVY-Amc (100 μM) in a reaction mixture containing 50 mM Hepes, pH 7.5, 1 mM DTT, 5 mM MgCl2, and 2 mM ATP. fluorescence of cleaved Amc was measured (excitation, 360 nm; emission, 470 nm).

Liquid Chromatography.

ULC/MS grade solvents were used for all chromatographic steps. Each sample was loaded using split-less nano-Ultra Performance Liquid Chromatography (10 kpsi nanoAcquity; Waters, Milford, Mass., USA). The mobile phase was: A) $H_2O$+0.1% formic acid and B) acetonitrile+0.1% formic acid. Desalting of the samples was performed online using a reversed-phase C18 trapping column (180 μm internal diameter, 20 mm length, 5 μm particle size; from Waters). The peptides were then separated using a HSS T3 nano-column (75 μm internal diameter, 250 mm length, 1.8 μm particle size; from Waters) at 0.35 μL/min. Peptides were eluted from the column into the mass spectrometer using the following gradient: 4% to 20% B in 80 min, 20% to 50% B in 25 min, 50% to 90% B in 5 minutes maintained at 90% for 5 min and then back to initial conditions.

Mass Spectrometry.

The nanoUPLC was coupled online through a nanoESI emitter (10 μm tip; New Objective; Woburn, Mass., USA) to a quadrupole orbitrap mass spectrometer (Q Exactive Plus, Thermo Scientific) using a FlexIon nanospray apparatus (Proxeon). Data was acquired in DDA mode, using a Top20 method. MS1 resolution was set to 70,000 (at 400 m/z), scan range 200 to 1,650 mz, automatic gain control 1e6 and maximum injection time was set to 20 msec. MS2 resolution was set to 17,500 and maximum injection time of 60 msec.

Data Processing.

Raw data was imported into either PEAKs Studio software version 7.0 or MaxQuant version 1.5.1.6. De novo sequencing and database search were conducted with the following parameters: mass error tolerance was set to 10.0 ppm and 0.02 Da (20 ppm for MaxQuant) for parent and fragment ions, respectively. Variable modifications were defined as oxidation (M) and deamidation (NQ). The database search was conducted against a canonical UniprotKB human database version 2015_07, supplemented with a list of common contaminants. A no enzyme or trypsin were defined for database search of the proteasome originated peptides or digested proteins fractions, respectively. The results were filtered using a 1% FDR at the peptide level.

Example 1

Isolation of Active Proteasomes from the Cells

A unique system of 'Proteasomal Profiling' was developed for the isolation of the active-degradome from the cell by purifying the proteasomal peptide pool, which represents proteins actively undergoing degradation at the time of experiment (FIG. 1). Proteasomal complexes were purified by immunoprecipitation using specific antibodies against the α6 subunit of the 20S core particle. To examine whether the catalytic activity of the proteasomes is retained during the purification procedures, an activity-based assay was performed using a fluorescent LLVY peptide substrate. Purified proteasomes degraded the LLVY substrate and this degradation was sensitive to the proteasome inhibitor MG132 (FIG. 2), indicating that using this protocol active proteasomes are efficiently isolated from cells.

Example 2

Protesomal Peptide Isolation

Figures 3A, 3B:
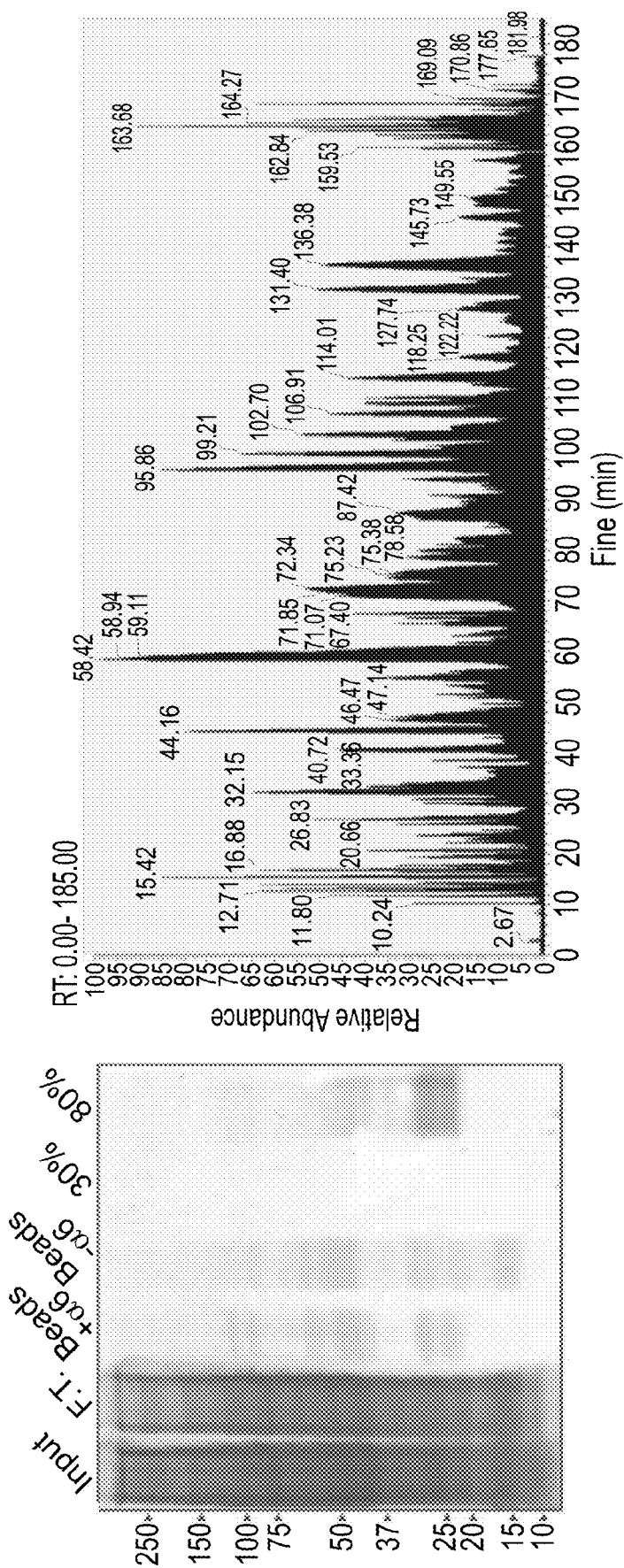
Figures 4A, 4B, 4C:
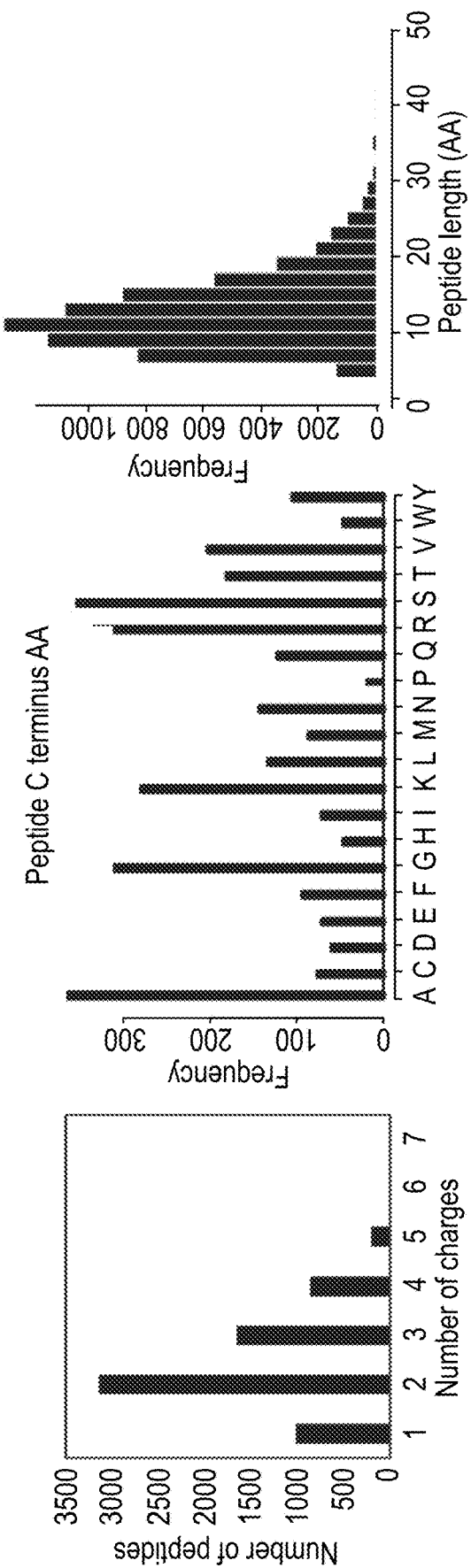

Previously described methods for identifying degraded proteins rely either on the detection of the level of the protein itself or on conventional MS analysis of proteins isolated with the proteasome following tryptic digest. These methods hold the disadvantages of being biased by protein abundance and the rate of turn-over and are most-likely the source of the lacking data regarding low-abundant and highly-turned over proteins. To overcome these difficulties, the present system was based on the identification of the actual peptides that are generated by the proteasome at a given point. To stabilize this pool of peptides, peptidases inhibitors were used to protect from degradation by peptidase upon exit from the proteasome, together with chemical cross-linkers that retain the generated peptides in the vicinity of the proteasome. Following treatment of cells with peptidase inhibitors and cross-linkers, proteasomes were immunoprecipitated using α6 antibodies and the immunocomplex was eluted. To separate the peptide pool of interest from all precipitated proteins, the differential sensitivity of peptides and proteins to acetonitrile was exploited. Peptides were eluted from the immunocomplex in 30% acetonitrile, while proteins were only released using 80% solution (FIG. 3A). Although peptides could not be visualized by this Coomassie staining it was important to appreciate that the eluted peptide fraction is clear of proteins, indicating that all peptides that are sent to analysis are indeed non-tryptic products. The eluted peptides fraction was then sent for MS analysis. The MS spectra generated by the present proteasomal profiling approach is rich with data from peptides that were generated without any exogenous trypsin, presenting a major breakthrough in MS analysis (FIG. 3B). Moreover, comparison of MS analysis data of peptides isolated by 'Proteasome Profiling' to data generated in conventional analysis of peptides following tryptic digest revealed unique and different properties exhibited by the identified peptides in number of charges, C-terminal amino acid composition, and peptide length (FIGS. 4A-C). These data designate 'Proteasome Profiling' as a novel method, independent of tryptic digest, for purifying proteasomal peptides with distinctive properties.

Example 3

MS Analysis and Characterization of the Degradome

To determine the efficiency of the 'Proteasome Profiling' system in identifying the target proteins, MS analysis was performed on the eluted fraction containing the isolated peptide pool. The analysis of predicted proteins originating from these peptides was then compared to conventional MS analysis of HeLa cells following tryptic digest. Specifically, the correlation between the relative numbers of identified proteins for each method with protein abundance was compared. The present results indicate that for identification of degraded proteins displaying average protein abundance, 'Proteasome Profiling' demonstrates similar efficiency to conventional MS (FIG. 5A). However, a dramatic increase of identified low-abundance proteins of 35% in 'Proteasome Profiling' versus 8% in conventional MS was observed (FIG. 5B). Additionally, a significant increase in the identification of extremely abundant proteins was also observed (FIG. 5C). These data therefore suggests that 'Proteasome Profiling' is highly advantageous in identifying proteins with both low (less than 10 ppm) and high (more than 500 ppm) abundance.

Figure 6A:
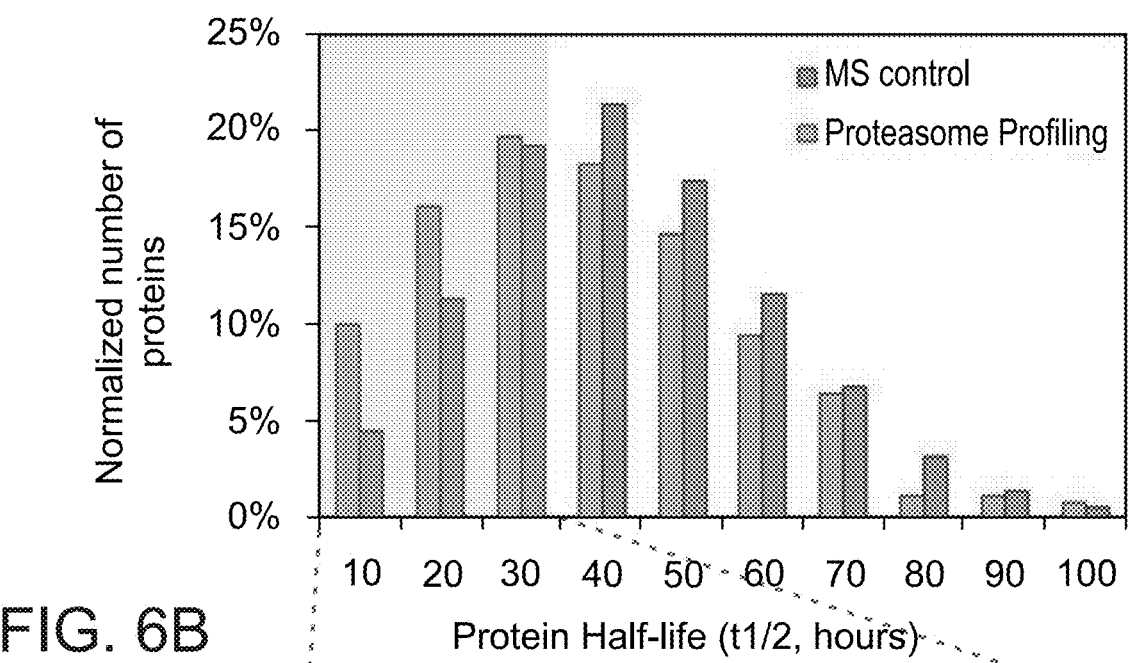
Figure 6B:
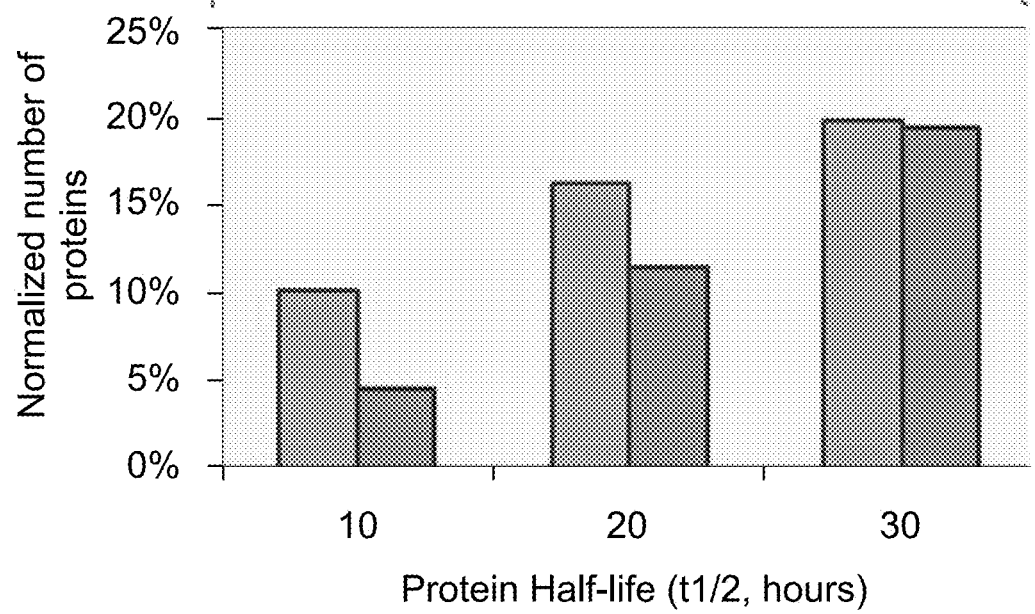

Next the present inventors determined the efficiency of the 'Proteasome Profiling' system in detecting short-lived proteins compared to conventional MS analysis. As shown in FIGS. 6A-B, using the 'Proteasome Profiling' system more short-lived proteins are identified, compared to conventional MS analysis (FIGS. 6A-B).

Moreover, functional annotation of the identified proteins revealed the 'Proteasome Profiling' enrichment of protein from several functional categories including transcription factors, receptors, nucleic-acid binding proteins, and more. Markedly, it is an established fact that several of these enriched groups are difficult to identify by conventional MS. Taken together, these data demonstrate the proficiency of 'Proteasome Profiling' to identify the 'active degradome' of the cell in an unbiased manner. 'Proteasome Profiling' presents an advantage over common methods by examining actual proteasomal substrates at the time of experiment, and importantly, allows for the first the detection of active degradation of short-lived and low-abundance proteins.

Example 4

Identification of Protesomal Peptides

Figure 7:
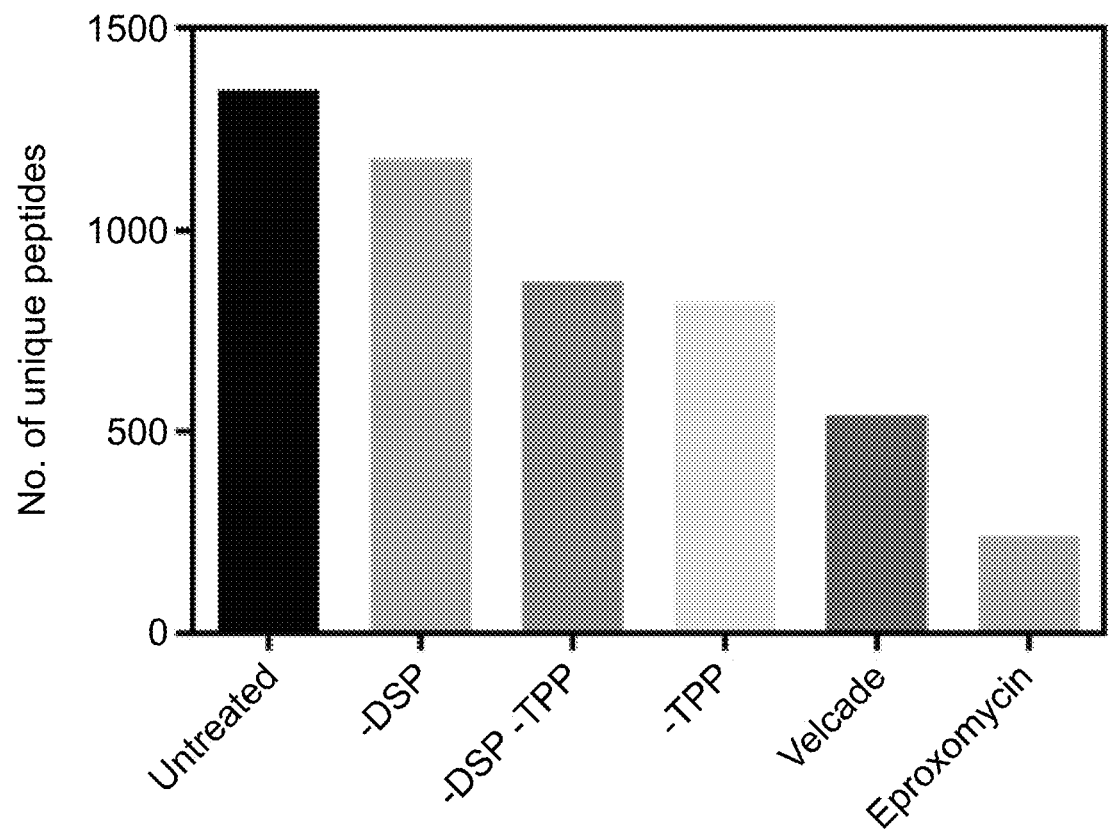

In an example analysis of HEK293 cell lysate using the 'Proteasome Profiling' the inventors identified 5,141 peptides (FIG. 7). The number of unique peptides was measured for the full treatment (denoted "untreated"), as well as for selected steps in the protocol such as for depletion of the crosslinker (denoted –DSP), for depletion of cellular proteases (denoted –TPP), or for both (denoted –DSP–TPP). The addition of proteasome inhibitors such as Velcade or Epoxomycin significantly reduced the number of identified peptide, suggesting that the 'Proteasome Profiling' detects the peptides which are processed by the proteasome itself or at its vicinity.

Figure 8:
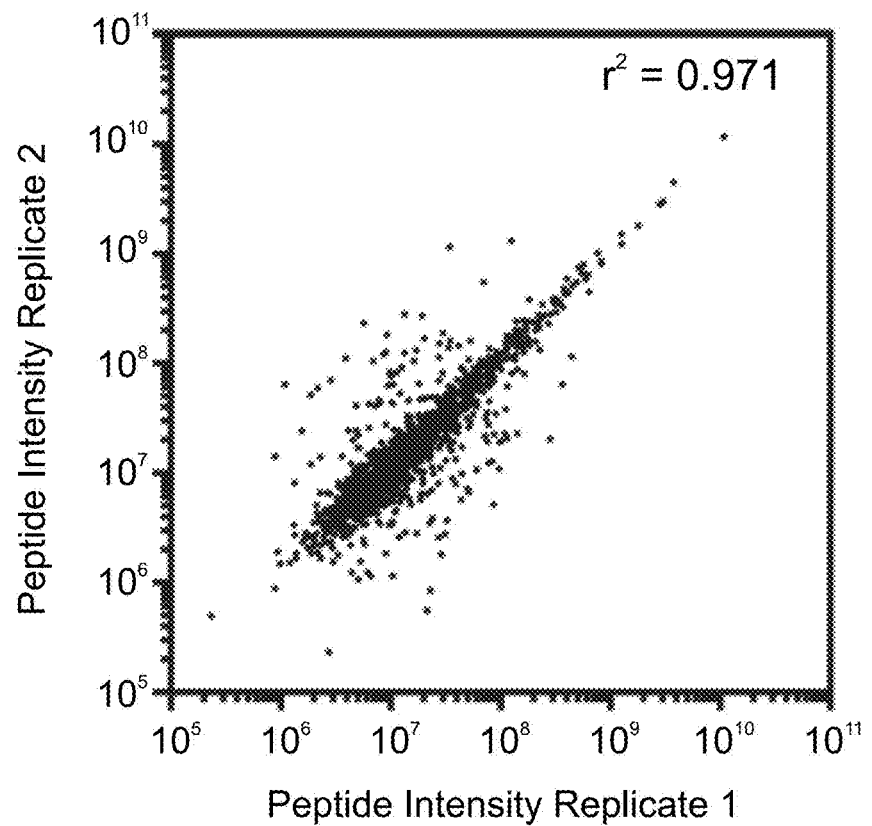
FIG. 8 shows the correlation of peptide intensities which are evident from the MS analysis. The data illustrates two biological replicates of HEK293 cell lysate.

The peptide intensity measurements between biological triplicates were highly reproducible, with correlation coefficient of $R^2=0.971$, as demonstrated in a dataset analyzing HEK293 cell lysate (FIG. 8, intensity is log transformed).

Figure 9:
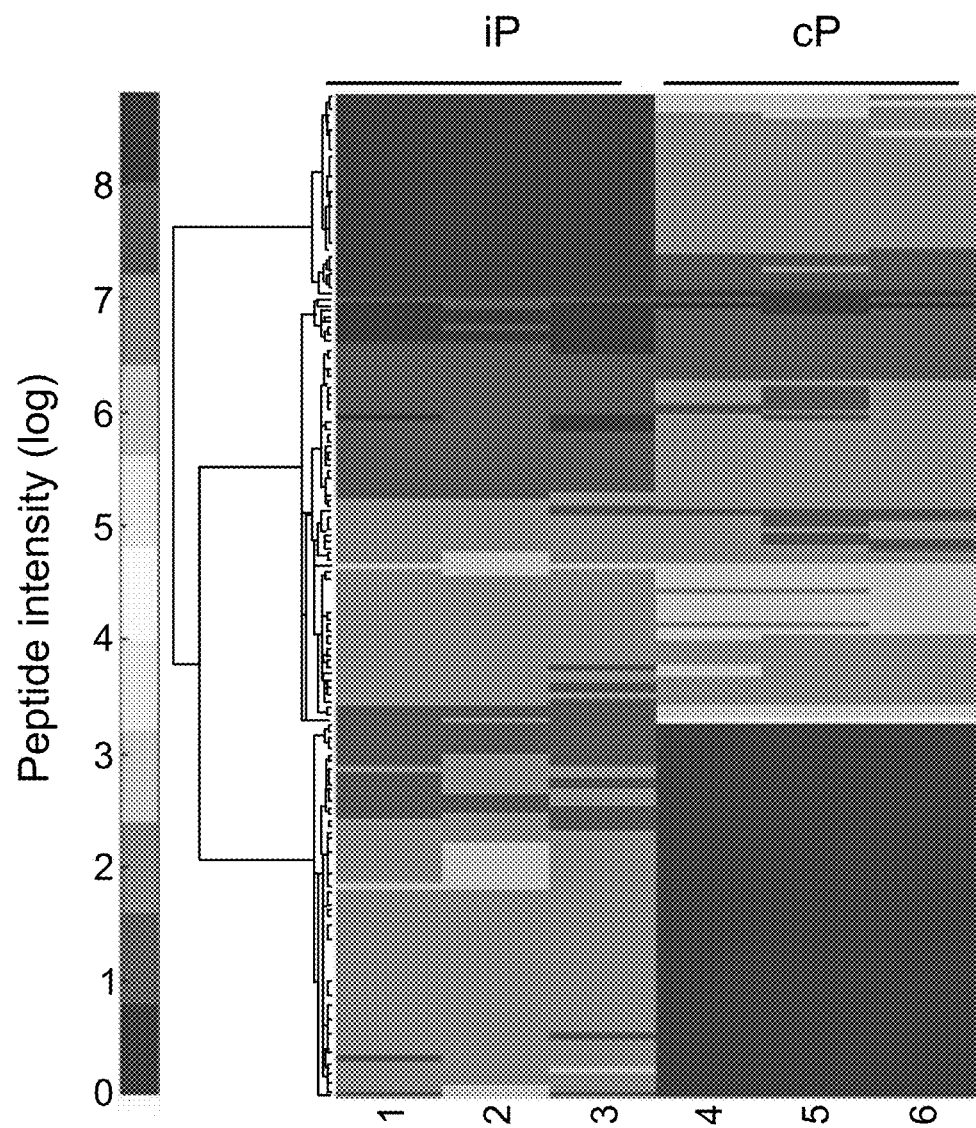
FIG. 9 shows clustering of the intensity of peptides which were immunoprecipitated from either immune-proteasomes (iP), pulled-down with anti-LMP2 antibodies, or from constitutive-proteasomes (cP) immunoprecipitated using anti-α6 antibodies, both from HEK293 cells (in triplicates).

The 'Proteasome Profiling' method revealed distinct degradation signatures of constitutive and immune proteasomes. FIG. 9 shows clustering the intensity of peptides which were immunoprecipitated from either immune-proteasomes (iP), pulled-down with anti-LMP2 antibodies, or from constitutive-proteasomes (cP) immunoprecipitated using α6 antibodies, from HEK293 cells (in triplicates).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of isolating barrel-like proteases, the method comprising isolating barrel-like proteases from a biological sample containing said barrel-like proteases under conditions that maintain the content of the barrel-like protease-processed peptides in said barrel-like proteases upon said isolation, thereby isolating the barrel-like proteases.

2. A method of isolating barrel-like protease-processed peptides, the method comprising:
    (a) isolating barrel-like proteases according to claim 1; and
    (b) isolating a peptide pool from total proteinaceous pool of said isolated barrel-like proteases, thereby isolating the barrel-like protease-processed peptides.

3. A method of identifying barrel-like protease-processed peptides, the method comprising:
    (a) isolating the barrel-like protease-processed peptides according to claim 2; and
    (b) subjecting the barrel-like protease-processed peptides to sequence analysis, thereby identifying the barrel-like protease-processed peptides.

4. The method of claim 1, wherein said conditions that maintain the content of the barrel-like protease-processed peptides in said barrel-like proteases comprise contacting the barrel-like proteases with a peptidase inhibitor.

5. The method of claim 1, wherein said conditions that maintain the content of the barrel-like protease-processed peptides in said barrel-like proteases comprise a cross-linking agent.

6. The method of claim 1, wherein said barrel-like protease is a proteasome.

7. The method of claim 1, wherein said biological sample is from a healthy tissue or cell, malignant tissue or cell, an inflamed tissue or cell, a senescent tissue or cell, an immature tissue or cell or a pathogen infected tissue or cell.

8. The method of claim 1, wherein said biological sample is selected from the group consisting of intact cells in suspension, tissue biopsy, cell-free proteasomes, exosomes and microparticles.

9. The method of claim 1, wherein said cell sample comprises a body fluid, a cell line or a primary cell.

10. The method of claim 9, wherein said body fluid is selected from the group consisting of whole blood, fractionated blood, serum, plasma, cerebrospinal fluid, urine, lymph fluid, an external secretion of the respiratory, intestinal and genitourinary tracts, tears, saliva, milk, peritoneal lavage and amniotic fluid.

11. The method of claim 1, wherein said biological sample comprises immune cells.

12. The method of claim 11, wherein said immune cells are antigen presenting cells.

13. The method of claim 1, wherein said biological sample comprises cancer cells.

14. The method of claim 1, wherein said biological sample comprises pathogen-infected cells.

15. The method of claim 1, wherein said isolating said barrel-like proteases is effected following cell lysis.

16. The method of claim 1, wherein said isolating said barrel-like proteases is effected by immunoprecipitation using an antibody to said barrel-like protease or a protein associated therewith.

17. The method of claim 2, wherein said isolating a peptide pool from total proteinaceous pool of said isolated barrel-like proteases is effected by solvent precipitation followed by solid phase extraction.

18. A barrel-like protease preparation obtainable according to the method of claim 1.

19. A peptide preparation obtainable according to the method of claim 2.

20. A method of testing an effect of a test compound or condition, the method comprising:
    (a) contacting a biological sample comprising barrel-like proteases with the test compound; and subsequently
    (b) identifying barrel-like protease processed peptides according to claim 3.

21. The method of claim 1, wherein said barrel-like protease-processed peptides are non-tryptic peptides.

22. The method of claim 2, wherein said barrel-like protease-processed peptides are non-tryptic peptides.

23. The method of claim 20, wherein said barrel-like protease-processed peptides are non-tryptic peptides.

* * * * *